(12) United States Patent
Miller (10) Patent No.: US 7,743,975 B2
(45) Date of Patent: Jun. 29, 2010

(54) INFUSION PUMP HAVING RADIOFREQUENCY IDENTIFICATION AND OPTICAL IMAGING CAPABILITIES

(75) Inventor: David Paul Miller, Brewerton, NY (US)

(73) Assignee: Jadak, LLC, North Syracuse, NY (US)

( * ) Notice: Subject to any disclaimer, the term of this patent is extended or adjusted under 35 U.S.C. 154(b) by 155 days.

(21) Appl. No.: 11/279,275

(22) Filed: Apr. 11, 2006

(65) Prior Publication Data

US 2007/0210157 A1    Sep. 13, 2007

Related U.S. Application Data

(63) Continuation-in-part of application No. 11/308,170, filed on Mar. 9, 2006.

(51) Int. Cl.
*G06K 7/00* (2006.01)
*G06F 17/00* (2006.01)

(52) U.S. Cl. ..................... 235/375; 235/486

(58) Field of Classification Search ............... 235/454, 235/375, 487, 486, 492; 710/8
See application file for complete search history.

(56) References Cited

U.S. PATENT DOCUMENTS

| | | | |
|---|---|---|---|
| 6,127,928 A * | 10/2000 | Issacman et al. | 340/572.1 |
| 6,501,382 B1 | 12/2002 | Rehufus et al. | |
| 2002/0038392 A1 * | 3/2002 | De La Huerga | 710/8 |
| 2002/0063622 A1 * | 5/2002 | Armstrong et al. | 340/10.31 |
| 2003/0095525 A1 | 5/2003 | Lavin et al. | |
| 2003/0132298 A1 | 7/2003 | Swartz et al. | |
| 2003/0135388 A1 * | 7/2003 | Martucci et al. | 705/2 |
| 2004/0118920 A1 | 6/2004 | He et al. | |
| 2004/0177032 A1 | 9/2004 | Bradley et al. | |
| 2005/0144044 A1 | 6/2005 | Godschall et al. | |
| 2005/0150959 A1 | 7/2005 | Izzo et al. | |
| 2005/0156040 A1 | 7/2005 | Young et al. | |
| 2005/0184160 A1 | 8/2005 | Steinmetz et al. | |
| 2005/0203941 A1 | 9/2005 | Polarine et al. | |
| 2005/0282603 A1 | 12/2005 | Parrot et al. | |
| 2006/0023930 A1 | 2/2006 | Patel et al. | |

FOREIGN PATENT DOCUMENTS

WO    WO2004059563    7/2004

* cited by examiner

*Primary Examiner*—Thien M Le
(74) *Attorney, Agent, or Firm*—David L. Nocilly; Bond Schoeneck & King, PLLC (57) ABSTRACT

An infusion pump including an optical imaging and an RFID reading module connected thereto through a host interface. The optical imaging and RFID module comprises a system microcontroller that interconnects an optical image capture subsystem and an RFID subsystem preferably routed through a single interface to the infusion pump. This infusion pump controls operation of the optical imaging and RFID module through commands provided through the interface and, as a result, capable of obtaining data encoded on barcodes and RFID tags. The infusion pump, through the optical imaging and RFID module, may thus automatically retrieve patient data, pharmacological information, dosage amounts, etc. from barcodes or RFID tags applied to the patient, intravenous medication, and even medical staff.

10 Claims, 6 Drawing Sheets

INFUSION PUMP HAVING RADIOFREQUENCY IDENTIFICATION AND OPTICAL IMAGING CAPABILITIES

CROSS-REFERENCE TO RELATED APPLICATION

The present application is a continuation-in-part of application Ser. No. 11/308,170, filed on Mar. 9, 2006.

BACKGROUND OF THE INVENTION

1. Field of Invention

The present invention relates to image capture and data collection systems and, more specifically, to a system and method for integrating radiofrequency identification and optical imaging with an infusion pump.

2. Description of Prior Art

Infusion pumps are important for the administration of intravenous (IV) therapy are designed to improve the accuracy and continuity of IV infusions by allowing nurses to program an hourly infusion rate and volume. Approximately 90% of hospitalized patients receive IV medications, a large portion of which are delivered by infusion pumps. Infusion pumps are often involved in one of the leading causes of medical injuries, referred to as adverse drug events. Most infusion pump-related errors occur because the pump is programmed with incorrect settings by the medical staff. For example, leaving out a decimal point or adding a zero when setting the infusion rate can easily result in a overdose. Alternately, infusion pumps may be inadvertently programmed to administer micrograms per kilogram per minute instead of micrograms per minute. Finally, there is no link at the bedside between the patient and type of drug being administered. Conventional infusion pumps thus lack the ability to independently verify the appropriateness of the manual programming performed by the medical staff to the patient at the bedside.

Recent attempts to overcome the limitations of infusion pumps involve the integration of "smart" infusion pumps with hospital patient and medical databases. Before using smart pumps at the bedside, a facility programs the pumps with its own specific data sets, or "profiles." These profiles specify the infusion requirements for different patient types and care areas, such as pediatric, adult, obstetrics, oncology, anesthesia, ICU, and post-anesthesia care units. Each profile includes a drug library that contains hospital-defined drug infusion parameters, such as acceptable concentrations, infusion rates, dosing units, and maximum and minimum loading and maintenance dose bolus limits, for 60 or more medications. The infusion pump will then alert the user if an infusion program is outside of recommended parameters, such as dosage, dosing unit (mcg/kg/min, units/hr, etc.), rate, or concentration. Although some infusion pumps are capable of communicating remotely with hospital databases, thereby avoiding the need for extensive programming prior to use, the risk associated with human entry of data remains.

SUMMARY OF THE INVENTION

It is a principal object and advantage of the present invention to provide a system and method for improving the safe use of infusion pumps.

It is an additional object and advantage of the present invention to provide a system and method for verifying the appropriateness of drug delivery performed by an infusion pump.

It is a further object and advantage of the present invention to provide a system and method for reducing the number of adverse drug events associated with the use of infusion pumps.

It is an additional object and advantage of the present invention to provide a system and method for automatically inputting data into an infusion pump.

Other objects and advantages of the present invention will in part be obvious, and in part appear hereinafter.

In accordance with the foregoing objects and advantages, the present invention comprises an infusion pump that includes an optical imaging and an RFID reading module connected thereto through a host interface. The module of the present invention comprises a system microcontroller that interconnects an optical image capture subsystem and an RFID subsystem through a single interface to a host computer. The system microprocessor is configurable via the infusion pump or an external host to selectively provide RFID reading or writing, optical imaging, barcode reading, or a variety of combinations of both techniques in combination with the infusion pump.

BRIEF DESCRIPTION OF THE DRAWINGS

The present invention will be more fully understood and appreciated by reading the following Detailed Description in conjunction with the accompanying drawings, in which.

DETAILED DESCRIPTION

Referring now to the drawings, wherein like numerals refer to like parts throughout, the present invention comprises an infusion pump including RFID and optical imaging capabilities. RFID and optical imaging capabilities are preferably provided via a combined RFID and optical imaging module that is interfaced with an infusion pump, or retrofit into an existing infusion pump, through a preexisting interface to provide RFID reading and optical imaging capabilities.

Figure 1:
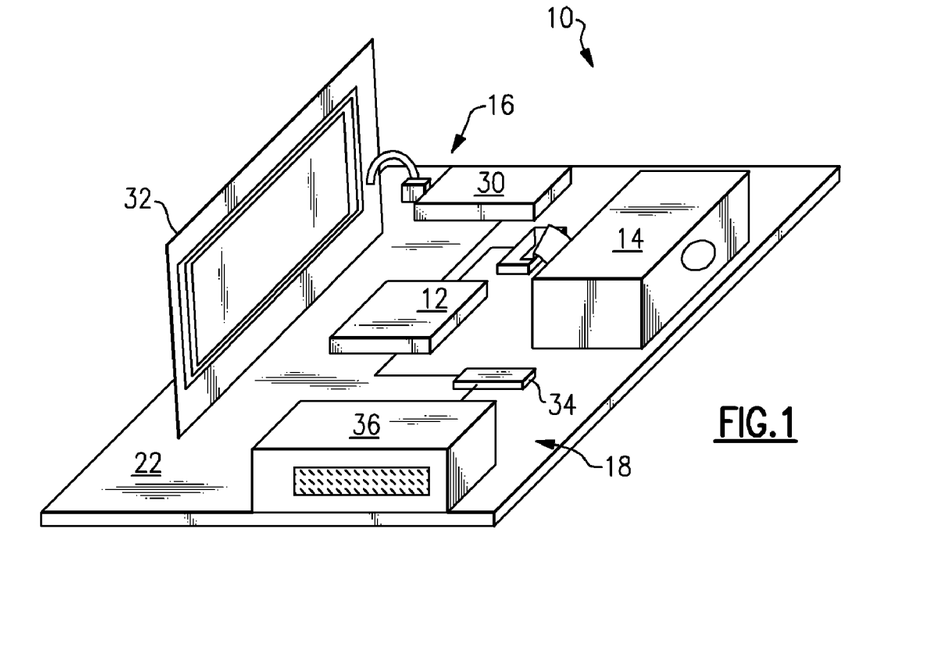
FIG. 1 is a perspective view of a combined RFID and optical imager module according to the present invention.

There is seen in FIG. 1 a combined RFID and optical image module 10 according to the present invention that may be used in connection with an infusion pump. Module 10 generally comprises a microcontroller 12 that interconnects a first submodule, such as an optical imager 14, and a second submodule, such as an RFID unit 16, to a single host interface 18. Alternatively, module 10 is capable of interconnecting any variety of data capturing devices as submodules and providing host controllability, including optical imagers, RFID transceivers, lasers, scales, thermometers or temperature probes, etc., in any variety of combinations. Module 10 may be arranged on a single printed circuit board 22 and encased as a single unit or housing. Integration of imager 14 and RFID unit 16 through interface 18 allows for combining control of operation of both submodules, such as RFID reading and barcode, through module 10, as will be explained in detail hereinafter.

Figure 2:
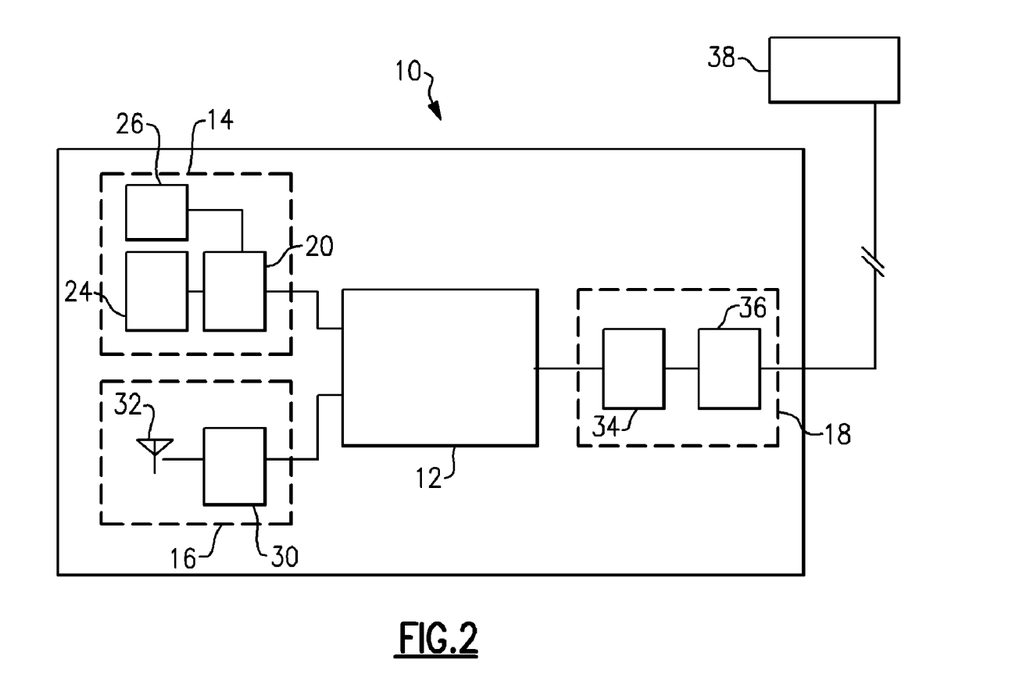
FIG. 2 is a schematic of a combined RFID and optical imager module according to the present invention.

Referring to FIG. 2, a first submodule of module 10 is illustrated as an optical imager 14 comprising an image engine 20 having image processing circuitry interconnected to microcontroller 12 for omni-directional optical scanning. Image engine 20 controls an image sensor 24, such as a complementary metal oxide semiconductor (CMOS) image sensor, and is capable of capturing two-dimensional images of 1D linear barcodes, 2D stacked/matrix barcodes, standard optical character recognition (OCR) fonts, Reduced Space Symbology (RSS) barodes, and postal barcodes, as well as providing image captured images for use in a wide range of applications, such as image and shape recognition, signature capture, image capture, and non-standard optical character recognition. Imager 14 may further include an illumination source 26 connected to engine 20, such as one or more light emitting diodes (LEDs) of various wavelengths, to enhance illumination, operation, and image capture. For example, module 10 may include red LEDs for general illumination and green LEDs for targeting. Imager 14 may comprise, but is not limited to, an IT4X10/80 SR/SF or IT5X10/80 series imager available from Hand Held Products, Inc. of Skaneateles Falls, N.Y. that is capable of scanning and decoding most standard barcodes including linear, stacked linear, matrix, OCR, and postal codes. Specifically, the IT5X10/80 series imager is a CMOS-based decoded output engines that can read 2D codes, and has image capture capabilities sufficient for use with module 10.

Imager 14 obtains an optical image of the field of view and, using preprogrammed algorithms in image engine 20, deciphers the context of the image to determine the presence of any decodable barcodes, linear codes, matrix codes, and the like. Image engine 20 may be programmed to perform other image processing algorithms on the image captured by imager 14, such as shape recognition, match filtering, and other high-level processing techniques. Alternatively, a captured image may be processed by microprocessor 12, albeit with a decreased level of performance due to the additional communication time needed to transfer images from image engine 20 to microprocessor 12.

Second submodule of module 10 may comprise an RFID unit 16 including an RFID transceiver 30 and associated RFID antenna 32 supporting standard RFID protocols, such as the TI Tag-it transponder protocol or ISO 15693. For these protocols, transceiver 30 operates at 13.56 MHz, and may comprise a S6700 Multi-Protocol Transceiver IC available from Texas Instruments of Dallas, Tex. Depending on the application, other frequency transceivers may be more appropriate based on target range, power availability, cost, etc. RFID unit 16 may further include a speaker or LED (not shown) for audibly indicating a successful interrogation of an RFID tag.

Antenna 32 is preferably a loop antenna of various sizes and turns implemented on a printed circuit board and connected to module 10, or a wire loop installed antenna installed directly onto module 10. Antenna 32 may be positioned remotely, thereby reducing the footprint of module 10 using an external connector, such as a MMCX coaxial connector. RFID transceiver 30 may be programmed to interrogate passive or active tags, process signals received from such tags (e.g., analog to digital conversion), and provide the information from the tags to microcontroller 12 for further processing or transmittal to a host computer via interface 18.

Host interface 18 comprises a host transceiver 34 and a host connector 36 for interconnection to a host device 38. Interface 18 may comprise a conventional RS232 transceiver and associated 12 pin RJ style jack. For example, an ADM202EARN available from Analog Devices, Inc. of Norwood, Mass. is a suitable RS-232/V.28 interface device having compliant levels of electromagnetic emissions and immunity. Alternatively, interface 18 may comprise other conventional buses, such as USB, IEEE 1394, I2C, SPI, or PCMCIA, or other connector styles, such as an FFC style to an embedded host or another module 10. Interface 18 may also comprise a wireless transceiver in lieu of connector 36 for wireless communication to a host computer. A Stewart Connector Systems Inc. SS-641010S-A-NF may serve as connector 36 for mating with a Stewart Connector 937-SP-361010-031 matching connector of a host device. Host interface 18 may also comprise a Molex MX52588 connector. Regardless of the type of connector 36 used, host transceiver 34 is programmed with the applicable protocols for interfacing with a host computer, such as USB, Bluetooth(r), and IrDA protocols. Transceiver 34 may also be programmed to support both non-inverted signal sense and inverted signal sense.

Microcontroller 12 comprises a conventional programmable microprocessor having on-chip peripherals, such as central processing unit, Flash EEPROM, RAM, asynchronous serial communications interface modules, serial peripheral interfaces, Inter-IC Buses, timer modules, pulse modulators with fault protection modules, pulse width modulators, analog-to-digital converters, and digital-to-analog converters. Additionally, the inclusion of a PLL circuit allows power consumption and performance to be adjusted to suit operational requirements. In addition to the I/O ports dedicated I/O port bits may be provided. Microcontroller 12 may further include an on-chip bandgap based voltage regulator that generates an internal digital supply voltage from an external supply range. Microcontroller 12 preferably comprises a Motorola MC9S12E128.

The functional integration of imager 14 and RFID unit 16 to interface 18 is accomplished by microcontroller 12, which receives and interprets host commands, and then executes the appropriate functions by driving imager 14 and/or RFID unit 16 accordingly. For example, the operation of imager 14 and RFID unit 16 may be triggered by serial commands sent to module 10 from a host device 38, or by a hardware button communicating directly with connector 36 or through host device 38. Microcontroller 12 may further be programmed to execute the functions otherwise performed by one or more of image engine 20, RFID transceiver 30, and host transceiver 34, thereby reducing the amount of circuitry and hardware required by module 10.

When integrating imager 14 and RFID unit 16, module 10 has three principle operational modes: image scanning using imager 14, tag interrogation using RFID unit 16, an interleaved mode that is a combination thereof, and a simultaneous mode. In imaging-only mode, module 10 will image and perform the applicable algorithms, such as barcode deciphering, until a barcode is detected or the device is un-triggered. In RFID-only, module 10 will interrogate until a tag is successfully read or module 10 is un-triggered. In interleaved mode, module 10 toggles between imaging and interrogation according to a predetermined timeout schedule. In simultaneous mode, module 10 causes simultaneous imaging and interrogation. In addition, module 10 may be programmed with timeouts to prevent hang-ups. As module 10 can receive, interpret, and execute host commands, these modes may be controlled by a user from host device 38.

Microcontroller 12 may direct RFID interrogation using RFID unit 16 in at least two modes. RFID unit 16 may operate in a free form mode that reads and writes data as a continuous stream, which is limited only by memory capacity. Once RFID unit 16 is triggered, depending on the mode, data is emitted from the serial port. Second, RFID unit 16 may operate in block mode, where a user may access individual blocks of information via commands sent through interface 18 and interpreted by microcontroller 12.

External control of module 10 is accomplished by a predefined protocol and set of serial host commands that are sent to module 10 from host device 38. The host commands are received by microcontroller 12, which executes the appropriate steps based on the content of the host command. For example, microcontroller 12 may be programmed to recognize host commands that trigger the activation of imager 14 and/or RFID unit 16. Host commands may also be defined to whether the data obtained from imager 14 and/or RFID unit 16 is stored locally in module 10 or passed through interface 18 to host device 38. Host commands may also be provided that enable the various scanning or imaging modes available from imager 14 and RFID unit 16, control the amount of time that imager 14 and RFID unit 16 will attempt scanning before timing out, direct the reading and writing of image and scan data, and select the location where the data is to be written. With regard to imager 14 and RFID unit 16, commands for opening and closing connections to image engine 20 and RFID transceiver 30, as well as commands that return the status of the connection are useful. For example, a host command received from host device 38 may trigger the capture of barcode or RFID data from imager 14 or RFID unit 16. When the scan is complete, a timeout occurs or triggering is turned off via a second host command, and the appropriate feedback is provided to host device 38. The host commands may be preprogrammed into microprocessor 12 and separately provided to host device 38 as a software package for controlling module 10. In addition, software for editing host commands may be supplied to host device 38 to allow a user to edit, add, or delete commands and the corresponding functionality.

Figure 3:
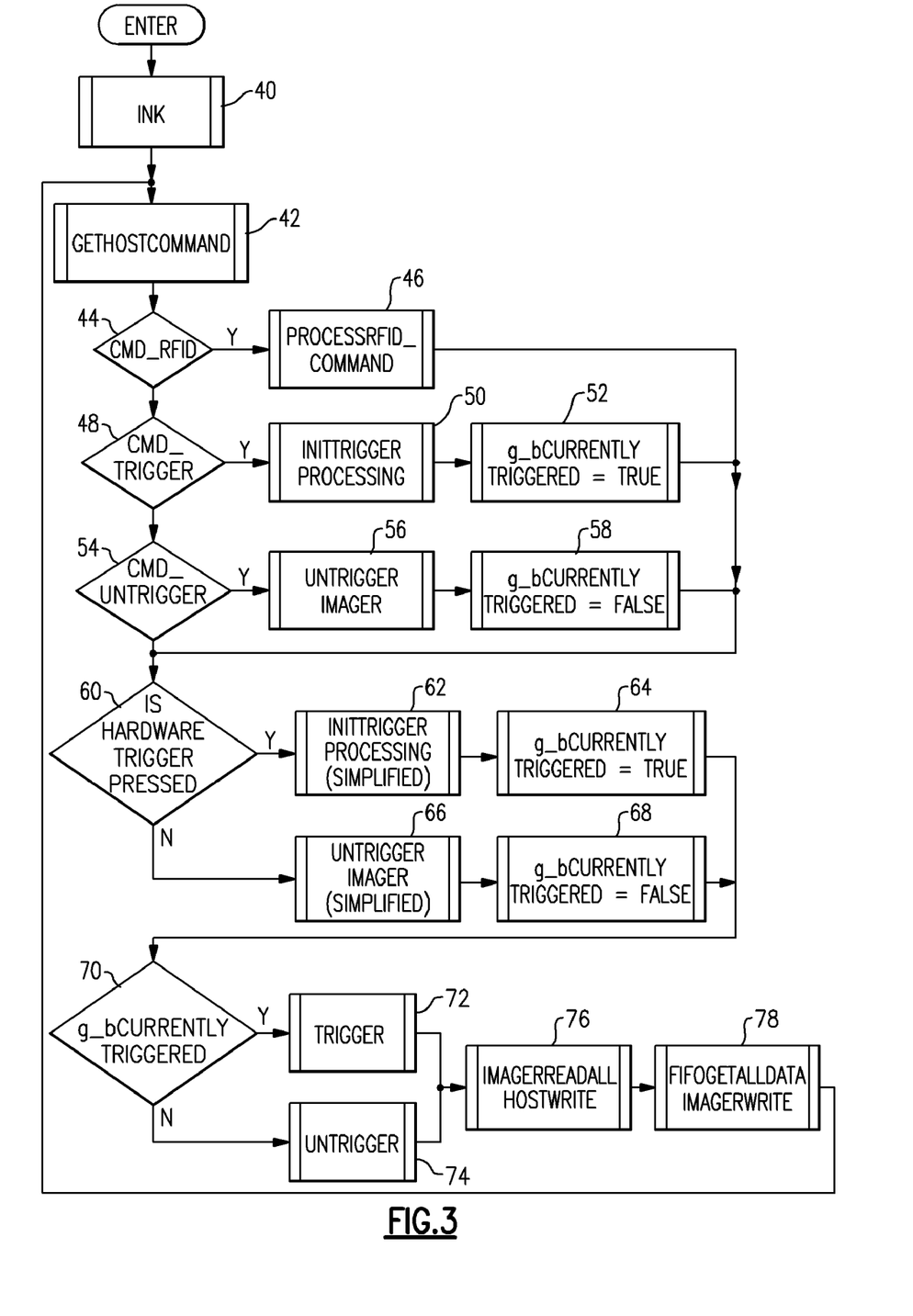
FIG. 3 is a flowchart of main-line processing of a combined RFID and optical imager module the according to the present invention.

FIG. 3 illustrates an embodiment of main-line host command processing in microprocessor 12 according to the present invention. The specific nomenclature used to define the various routines may be varied by the user or software developer provided that the appropriate functions are performed, and any number of routines and subroutines may be defined and executed in various orders to accomplish image and RFID reading and processing according to the present invention. After initialization 40, microcontroller 12 runs a routine, referred to as GetHostCommand 42, to check whether a host command has been received from host device 38. Upon receipt of a host command, microprocessor 12 checks whether the command is an RFID control command, CMD_RFID 44. If so, the command is processed by routine ProcessRFID_Command 46. If not, a check is performed to see whether the command is an trigger command, CMD_TRIGGER 48. If the command is a trigger command, the appropriate instruction are processed to initiate triggering, InitTriggerProcessing 50 and a variable, referred to as CurrentlyTriggered 52, is assigned the value of TRUE or FALSE depending on whether the selected device has already been triggered. If the command is not a trigger command, a check is performed to see whether the command is an untrigger command, CMD_UNTRIGGER 54. If the command is an untrigger command, the appropriate steps are taken to stop triggering, UnTriggerImager 56, and a variable, CurrentlyTriggered 58, is assigned the value of TRUE or FALSE depending on whether the selected device has already been triggered.

After any of the above processing, microprocessor 12 checks to see whether a hardware trigger has been pressed 60, the triggering processing is performed, InitTriggerProcessing 62, and a variable, referred to as CurrentlyTriggered 64, is assigned the value of TRUE or FALSE depending on whether the selected device has already been triggered. If a hardware trigger has not been pressed 60, the appropriate instruction are processed to stop triggering, UnTriggerImager 66, and a variable, referred to as CurrentlyTriggered 68, is assigned the value of TRUE or FALSE depending on whether the selected device has already been triggered. Finally, microprocessor checks to see whether the CurrentlyTriggered variable is TRUE or FALSE 70, and then calls function Trigger 72 or function UnTrigger 74 as appropriate. Data is then read from imager 14 and written to the host, ImagerReadAllHostWrite 76, and host data that should be routed to imager 14 is written to it, FifoGetAllDataImagerWrite 78.

Figure 4A:
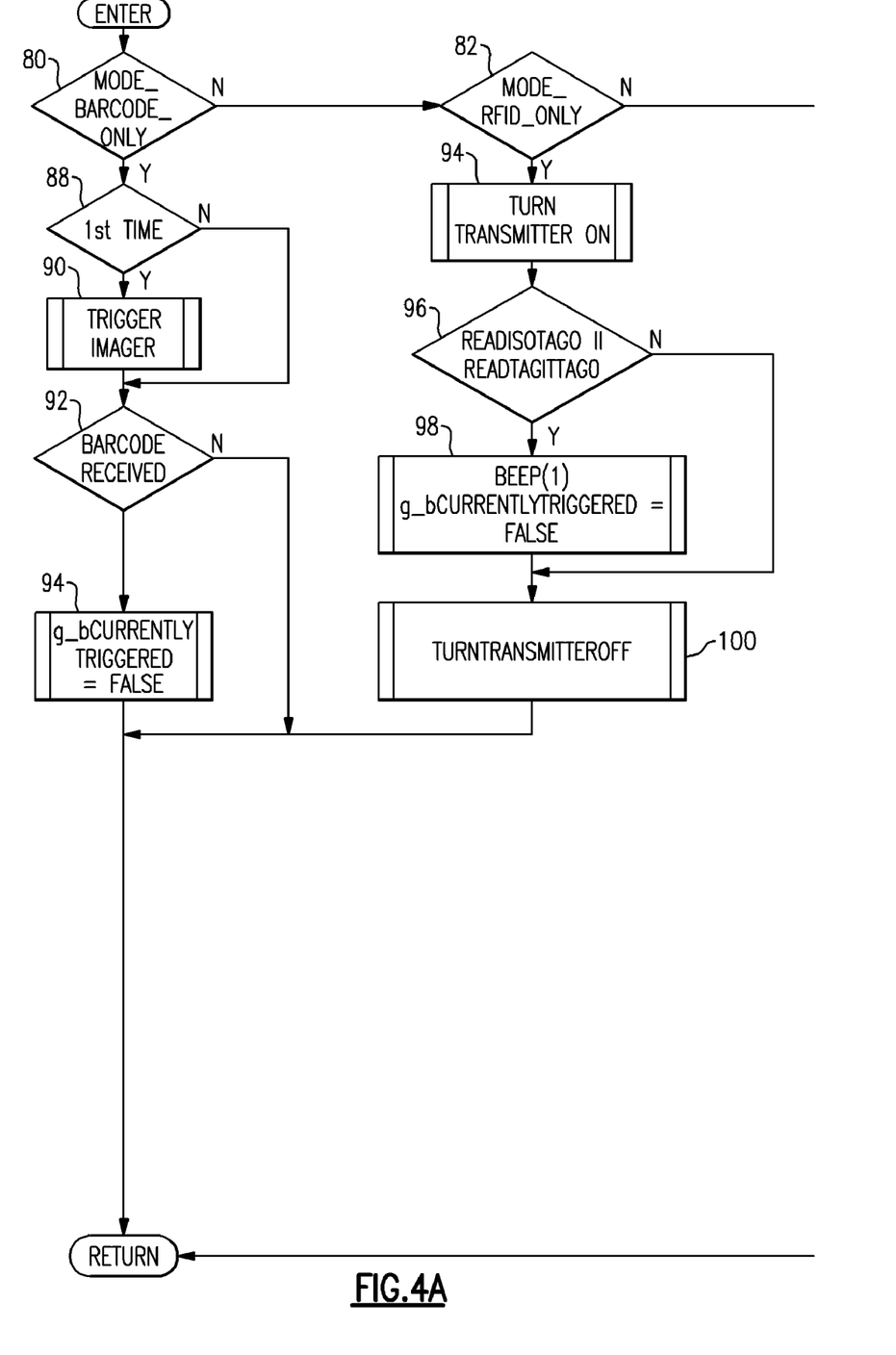
FIGS. 4A and 4B are flowcharts of trigger command processing in a combined RFID and optical imager module according to the present invention.
Figure 4B:
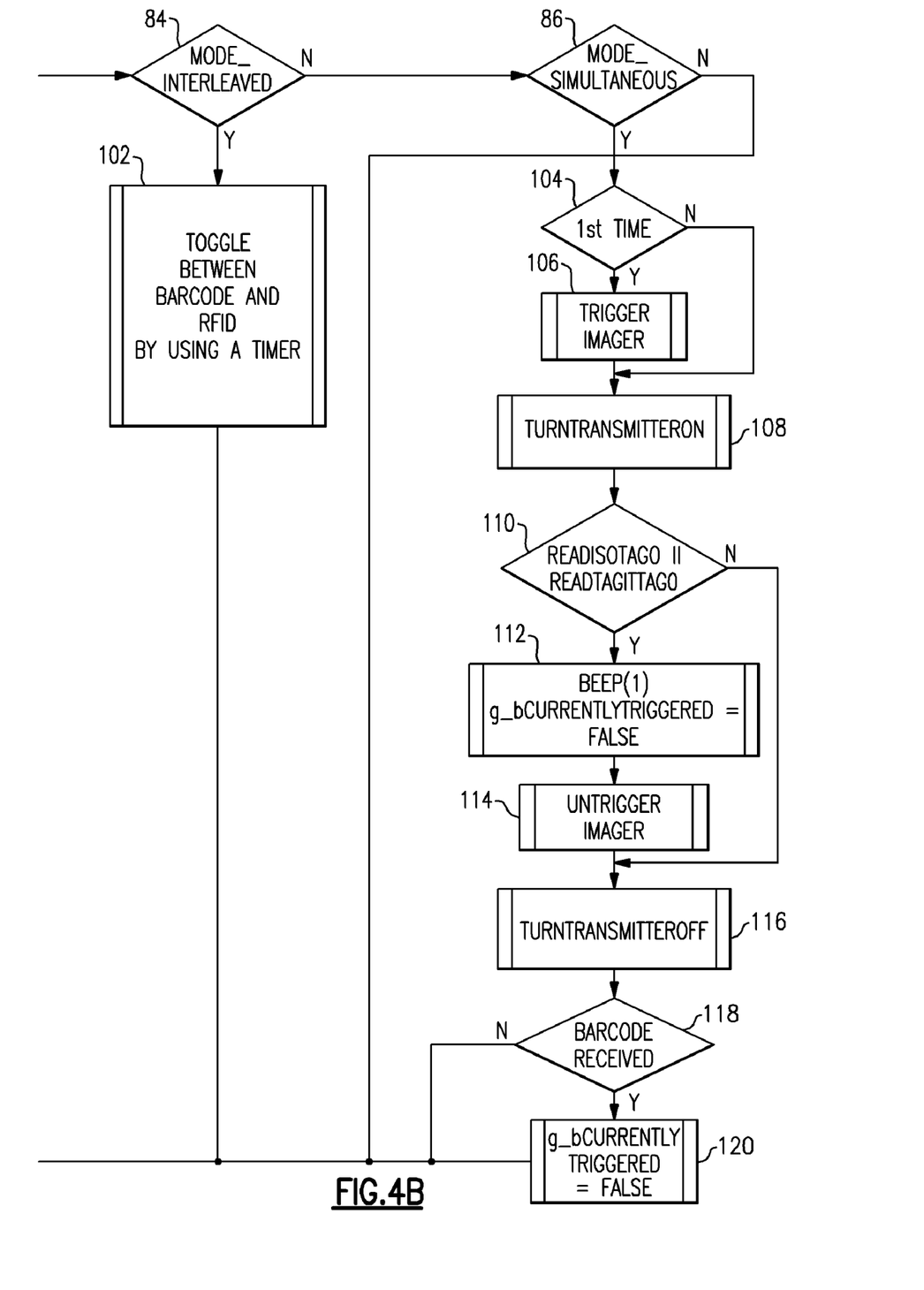

There is seen in FIGS. 4A and 4B, trigger host command processing in microprocessor 12 according to the present invention. Upon receipt of a trigger command, microcontroller 12 first checks to see whether barcode only scanning 80, RFID only scanning 82, interleaved RFID and barcode scanning 84, or simultaneous RFID and image scanning 86 has been previously selected. If bar code only scanning 80 has been selected for the first time 88, and since InitTriggerProcessing 50 has been called, microcontroller 12 triggers imaging 90. If an image is successfully captured and applicable information successfully extracted from the image 92, such as barcode, microcontroller 12 assigns FALSE to the variable CurrentlyTriggered 94. If RFID only scanning 82 has been selected, microcontroller 12 turns the RFID transmitter on 94. If an RFID tag is successfully read 96, an audible tone is sounded and microcontroller 12 sets variable CurrentlyTriggered to FALSE 98. Microcontroller 12 turns transmitter off 100. If interleaved RFID and barcode scanning 84 has been selected, microcontroller 12 toggles operation of imager 14 and RFID unit 16 using a timer 102. If simultaneous RFID and image scanning 86 has been selected, microcontroller 12 checks to see whether the triggering is for the first time 104 and, if so, triggers the imager 106. Transmission from the RFID unit 16 is also turned on 108, and a nearby RFID tag is read 110. If the reading of tag 110 is successful, an audible tone is sounded and variable CurrentlyTriggered is set to FALSE 112. Imager 14 is also untriggered 114 and the transmitter is turned off 116. If the image is successfully processed, e.g., a barcode is received 118, and variable CurrentlyTriggered is set to FALSE 120.

Figure 5:
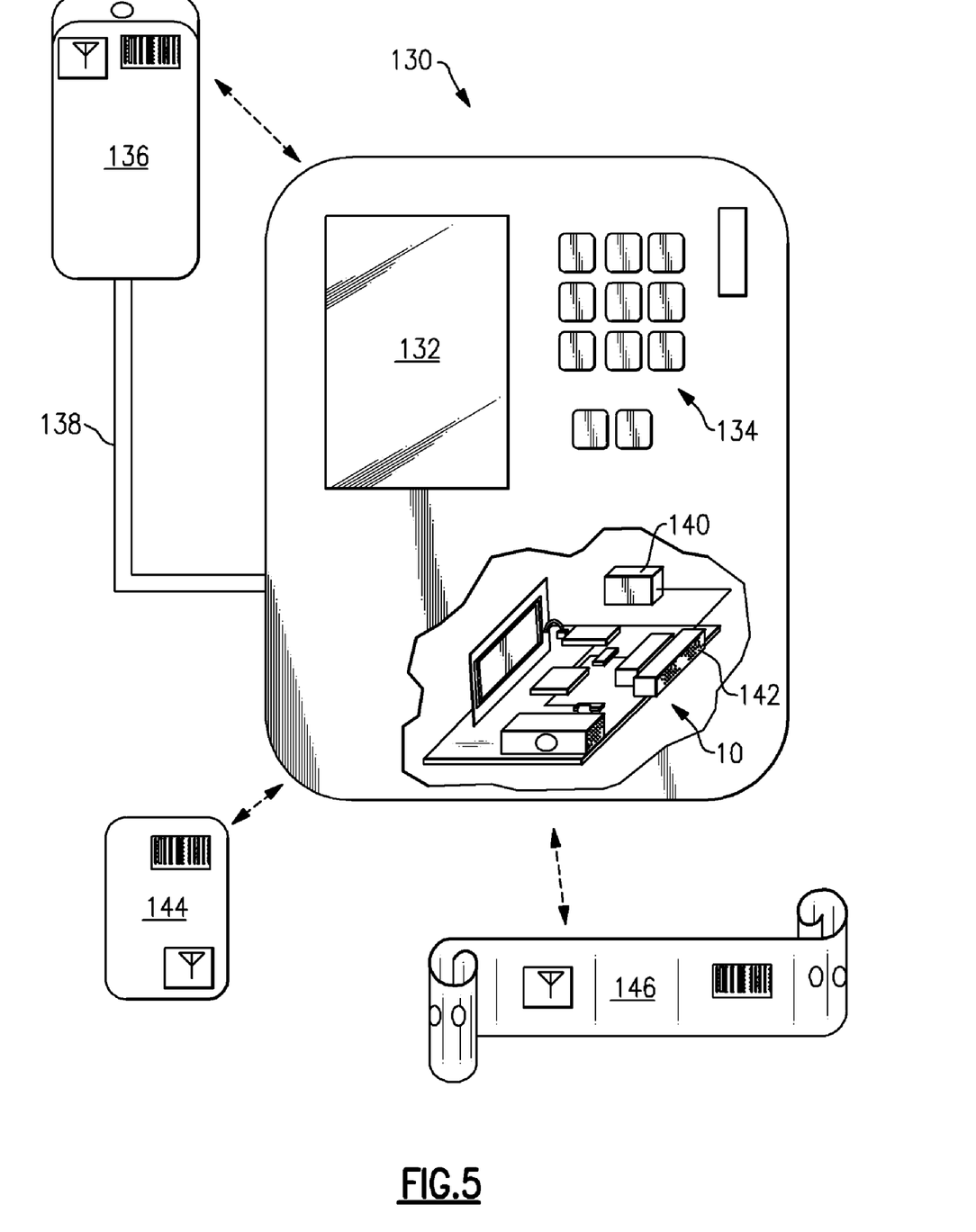
FIG. 5 is a schematic of an infusion pump according to the present invention.

There is seen in FIG. 5, an infusion pump 130 comprising a display screen 132 for visually presenting status or programming information and a keypad 134 or keyboard associated therewith for manual entry of data by medical personnel. Infusion pump 130 controls the delivery of fluid medication from an intravenous bag 136 through tubing 138 to a patient (not shown). Infusion pump 130 further comprises a microcontroller 140 for controlling the various operations and functionality of infusion pump 130. Infusion pump 130 also comprises a combined RFID and imaging module 10 associated therewith. Preferably, module 10 is provided within pump 130 and interconnected to microcontroller 140 via a connector 142 that mates with connector 36 of host interface 18. Thus, microcontroller 140 of pump 130 acts as a host device, as explained above, and is programmed to provide host commands to module 10, thereby controlling operation of optical imager 14 and RFID unit 16. Module 10 is positioned within pump 130 so that imager 14 is flush with the housing of pump 130, or so that all or a portion of imager 14 extends outwardly from pump 130, such that object may be presented to imager 14 and one or images thereof may captured by imager 14.

Imager 14 may capture and decode barcode information contained on IV bag 136, a badge 144, or even a patient wristband 146. As module 10 also includes RFID unit 16, information may be additionally stored on IV bag 136, badge 144, and patient wristband 146 for interrogation by RFID unit 16. Thus, infusion pump 130 may be automatically provided with all of the information necessary to safely and securely verify that the proper medication is being given to the patient in the appropriate, prescribed dosages and rates.

Figure 6:
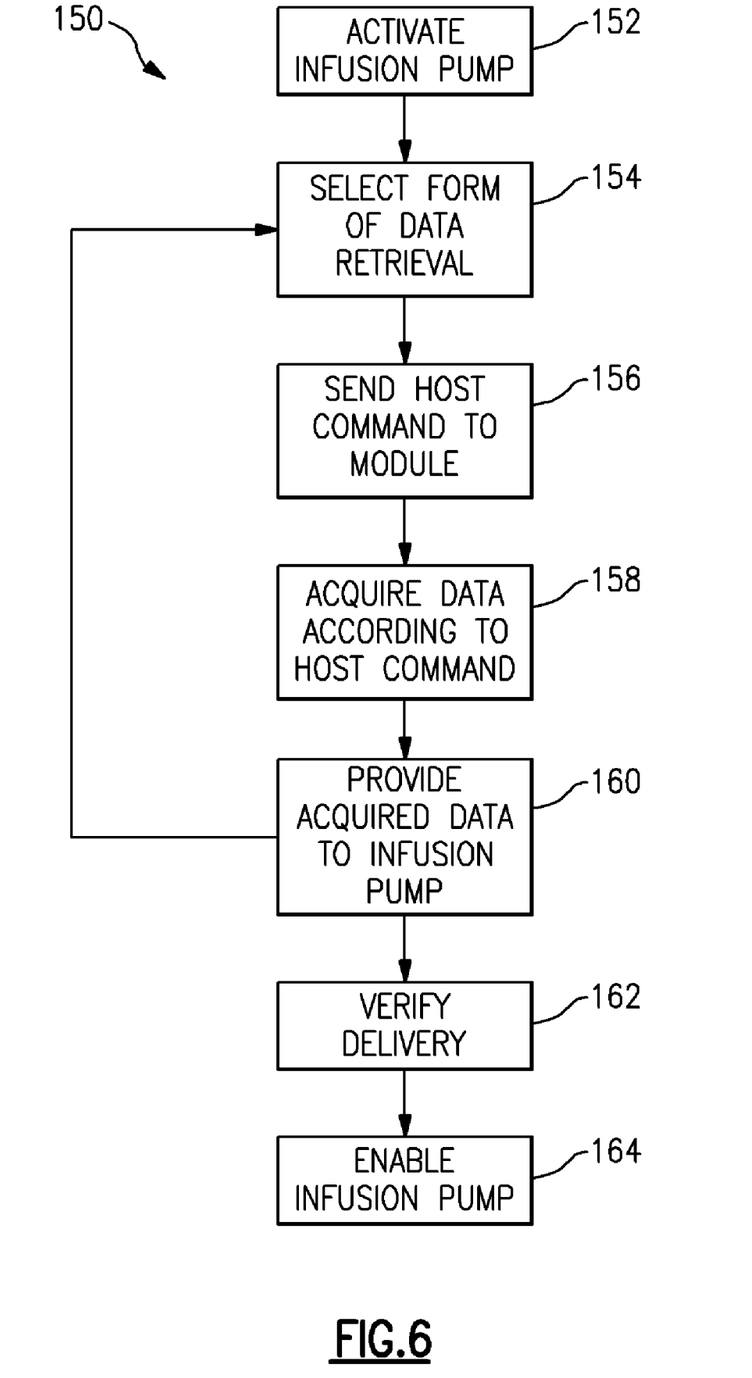
FIG. 6 is a flowchart of control processing in infusion pump according to the present invention.

A sample control process 150 for pump 130 is illustrated in FIG. 6. More particularly, infusion pump 130 is first activated 152 by a medical worker, such as by turning on infusion pump 130. Next, the form of data retrieval is selected 154, e.g., optical imaging/barcode and/or RFID. The format may be preprogrammed into microcontroller 140, or manually selected by use of keypad 134. After selection 154, the appropriate host command is sent 156 to module 10 by microcontroller 140. As described above, host commands controlling operation of module 10 may be supplied to a host device, such as infusion pump 130, as software that is loadable onto microcontroller 140. Next, data is acquired according to the host command 158 using imager 14 or RFID unit 16. Successfully acquired data is then provided 160 by module 10 to infusion pump 130 via host interface 18 to microcontroller 140 using the appropriate protocols. If any additional data is to be automatically provided to infusion pump 130, steps 154-160 may be repeated for each object from which data is to be acquired. Microcontroller 140 then verifies that delivery is proper 162 by considering the data acquired by module 10, and infusion pump 130 is enabled for delivery of medication to the patient.

Verification of delivery 162 encompasses any number of checks. For example, microcontroller 140 may receive information about the particular medicine to be dispensed from bag 136, about the individual who is authorizing the delivery of the medicine from badge 144, and about the patient who will be receiving the medication from wristband 146, whether by capturing optical images of identification objects containing indicia, such as barcodes, or data stored within identification objects, such as RFID tags. Microcontroller 140 may then retrieve the patient's electronic medical records from the hospital's electronic medical records database, whether copied and stored locally or accessed remotely through a hospital-wide network, and compare the stored information with the acquired information to ensure that the IV medications were actually ordered for the patient, and to confirm when the patient is scheduled to receive the medication. Microcontroller 140 can also verify the identity of the medical worker who is activating the infusion pump to ensure that the person is authorized to dispense the particular medication. Microcontroller 140 can further cross-check the prescribed dosage for the particular medication against stored medical records containing the proper dosages and infusion rates for particular medications. Only after some or all of these checks are performed will infusion pump 130 be enabled 164 to deliver medicine to the patient.

What is claimed is:

1. A medical device, comprising:
    a first microcontroller programmed to send host commands;
    a module comprising a printed circuit board;
    a host interface positioned on said circuit board and attached to said first microcontroller for receiving said host commands;
    a second microcontroller positioned on said circuit board and interconnected to said first microcontroller through said host interface that is programmed to be responsive to said host commands to retrieve data from an object presented to said medical device;
    said module further including an optical imager and an RFID transceiver connected to said second microcontroller, wherein said second microcontroller controls operation of both of said optical imager and said RFID transceiver based on receipt of said host commands.

2. The device of claim 1, wherein said second microcontroller controls operation of said optical imager and said RFID transceiver based on receipt of said host commands.

3. A method of controlling an infusion pump, comprising the steps of:
    presenting an object including data encoded therein to said medical device;
    sending a command from a first microcontroller positioned in said infusion pump through a host interface mounted on a printed circuit board and interconnected to said first microcontroller to a second microcontroller positioned on said circuit board that is programmed to retrieve data from said object based upon said command;
    retrieving said data from said object in a manner indicated by said command;
    comparing said data against data stored in a database; and
    enabling said medical device after comparing said data retrieved from said object to data stored in said database.

4. The method of claim 3, wherein said data is retrieved from said object by capturing an optical image of said object and decoding information present within said image.

5. The method of claim 4, wherein said information present within said image is a barcode.

6. The method of claim 3, wherein said data is retrieved from said object by interrogating said object with an RFID transceiver.

7. The method of claim 6, wherein said object is an RFID tag.

8. In an infusion pump including a first microcontroller for delivering fluids to a patient, the improvement comprising:
    a printed circuit board having a host interface positioned thereon;
    an optical imager positioned on said circuit board for obtaining an image of an object presented to said infusion pump;
    a radiofrequency identification (RFID) transceiver positioned on said circuit board for obtaining data from an RFID tag presented to said infusion pump;
    a second microcontroller positioned on said circuit board and attached to said optical imager and said RFID transceiver, wherein said second microcontroller interconnected to said first microcontroller of said infusion pump via said host interface, wherein said first microcontroller is programmed to transmit host commands to said second microcontroller, and wherein said second microcontroller is programmed to operate both of said optical imager and said RFID transceiver in response to said host commands.

9. The infusion pump of claim 8, wherein said second microcontroller is programmed to extract information from said image and said data and transmit a message to said first microcontroller reflecting the information extracted from said image and said data.

10. The infusion pump of claim 9, wherein said first microcontroller selectively permits the use of said infusion pump based upon the message received from said second microcontroller.

* * * * *